US012678602B2

(12) United States Patent　　(10) Patent No.:　US 12,678,602 B2
Fuseya　　(45) Date of Patent:　Jul. 14, 2026

(54) DILATOR

(71) Applicant: ASAHI INTECC CO., LTD., Seto (JP)

(72) Inventor: Yukihiro Fuseya, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 494 days.

(21) Appl. No.: 18/115,045

(22) Filed: Feb. 28, 2023

(65) Prior Publication Data

US 2023/0201547 A1　　Jun. 29, 2023

Related U.S. Application Data

(63) Continuation of application No. PCT/JP2020/033397, filed on Sep. 3, 2020.

(51) Int. Cl.
　　*A61M 29/00*　　(2006.01)
　　*A61M 25/00*　　(2006.01)
(52) U.S. Cl.
　　CPC ........ *A61M 29/00* (2013.01); *A61M 25/0052* (2013.01)
(58) Field of Classification Search
　　CPC .. A61M 29/00; A61M 29/02; A61M 25/0052; A61M 25/01; A61B 17/34
　　See application file for complete search history.

(56) References Cited

U.S. PATENT DOCUMENTS

| | | | | |
|---|---|---|---|---|
| 10,321,933 B1 * | 6/2019 | Ramee | ................... | A61M 39/06 |
| 2013/0190801 A1 * | 7/2013 | Divino | ..................... | A61F 2/01 |
| | | | | 606/200 |

| | | | | |
|---|---|---|---|---|
| 2019/0126005 A1 * | 5/2019 | White | ............... | A61M 25/0021 |
| 2020/0016384 A1 | 1/2020 | Fuseya et al. | | |
| 2020/0016385 A1 | 1/2020 | Fuseya et al. | | |
| 2020/0016386 A1 | 1/2020 | Fuseya et al. | | |
| 2020/0016387 A1 | 1/2020 | Fuseya et al. | | |
| 2020/0338625 A1 | 10/2020 | Kageyama | | |
| 2021/0001097 A1 | 1/2021 | Fuseya et al. | | |
| 2021/0001098 A1 | 1/2021 | Fuseya et al. | | |
| 2022/0288365 A1 | 9/2022 | Fuseya et al. | | |

FOREIGN PATENT DOCUMENTS

| | | | | |
|---|---|---|---|---|
| JP | 2013-165926 A | 8/2013 | | |
| JP | 2018167050 A * | 11/2018 | ......... | A61B 17/3417 |
| JP | 2019-107326 A | 7/2019 | | |
| JP | 6588679 B1 | 10/2019 | | |

* cited by examiner

*Primary Examiner* — Elizabeth Houston
(74) *Attorney, Agent, or Firm* — Oliff PLC

(57)　　　ABSTRACT

A dilator includes a distal end side coil part, and a proximal end side coil part located at a proximal end side of the distal end side coil part and having a distal end portion connected to a proximal end portion of the distal end side coil part. The distal end side coil part includes a first coil having a wire wound in a first winding direction, and a second coil provided on an outer periphery of the first coil and having a wire wound in a second winding direction that is opposite to the first winding direction. The proximal end side coil part includes a third coil having a wire wound in the second winding direction, and a fourth coil provided on an outer periphery of the third coil and having a wire wound in the first winding direction.

9 Claims, 3 Drawing Sheets

DILATOR

CROSS REFERENCE TO RELATED APPLICATION

This application is a continuation application of International Application No. PCT/JP2020/033397, filed Sep. 3, 2020. The contents of this application are incorporated herein by reference in their entirety.

BACKGROUND

This disclosure relates to a dilator.

In medical treatment such as endoscope inspection, a medical device used by being inserted to a body cavity is used. Japanese Patent Application Publication No. 2019-107326 discloses a medical device formed of a hollow twisted wire. This hollow twisted wire includes a first layer and a second layer and is configured such that a twisting direction of a wire in the first layer and a twisting direction of a wire in the second layer are opposite to each other.

SUMMARY

A dilator that expands a hole formed in a wall of the alimentary canal or the like of a patient for treatment is known. A hole is expanded by aligning a distal end of the dilator with a hole formed in a wall and pushing a tapered portion of the distal end into the hole. In a case where the hollow twisted wire including two layers disclosed in Patent Literature 1 is applied to a dilator, an inner layer contracts and an outer layer expands depending on a rotation direction of the dilator, so that the two layers do not make contact with each other and sufficient torquability may not be obtained.

One object of the present disclosure is to provide a dilator capable of obtaining high torquability irrespective of a rotation direction.

A dilator according to one aspect of the present disclosure includes: a distal end side coil part and a proximal end side coil part. The distal end side coil part includes a first coil having a hollow shape and including a first wire wound in a first winding direction and a second coil provided on an outer periphery of the first coil and including a second wire wound in a second winding direction that is opposite to the first winding direction. The proximal end side coil part is located at a proximal end side of the distal end side coil part and having a distal end portion connected to a proximal end portion of the distal end side coil part. The proximal end side coil part includes a third coil having a hollow shape and including a third wire wound in the second winding direction; and a fourth coil provided on an outer periphery of the third coil and including a fourth wire wound in the first winding direction.

DETAILED DESCRIPTION

Hereinafter, embodiments of the present disclosure will be described with reference to the drawings. The size of the dilator in each drawing is a size illustrated to facilitate understanding of the embodiments, and does not correspond to the actual size.

In this specification, the "distal end side" indicates a side along the longitudinal direction of the dilator (a direction along an axial direction of the dilator) in which a distal end side coil part is located with respect to a proximal end side coil part. The "proximal end side" indicates a side along the longitudinal direction of the dilator that is opposite to the distal end side. Moreover, the "distal end" indicates an end part on the distal end side of an arbitrary member or portion, and the "proximal end" indicates an end part on the proximal end side of an arbitrary member or portion.

Figure 1:
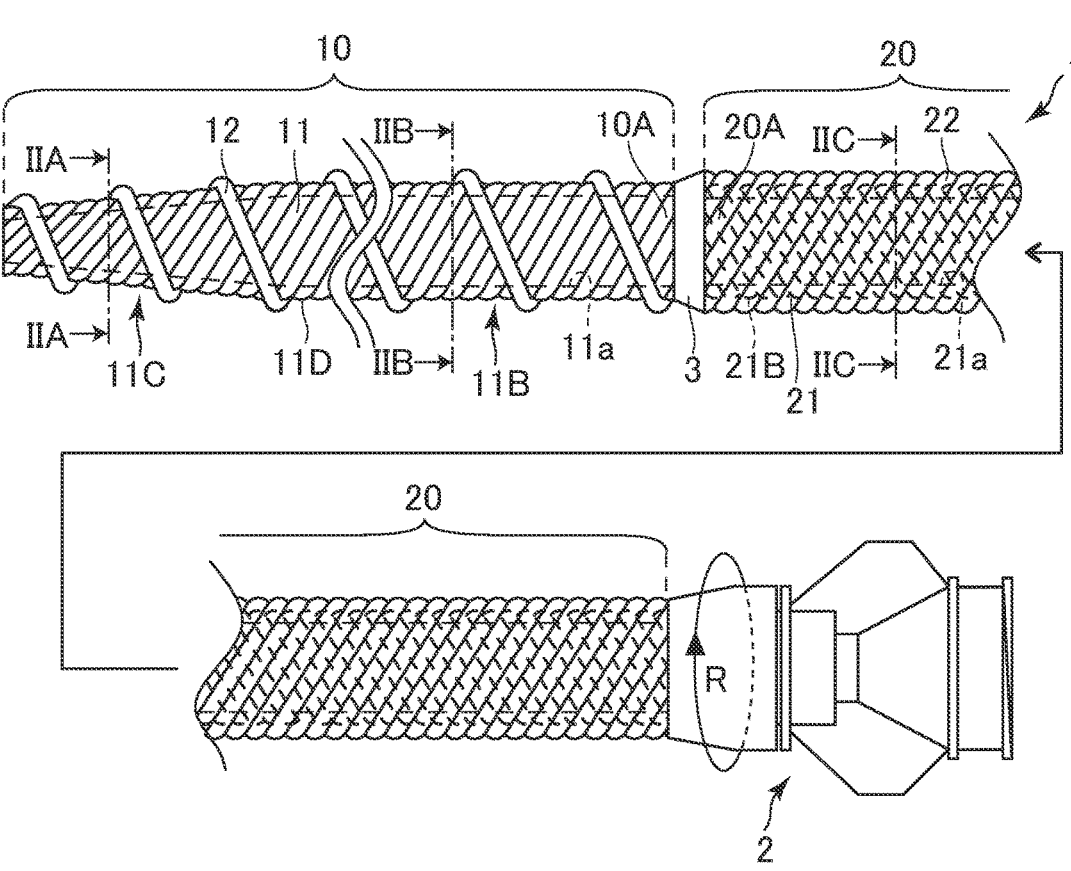
FIG. 1 is an overall configuration diagram of a dilator according to an embodiment.
Figure 2A:
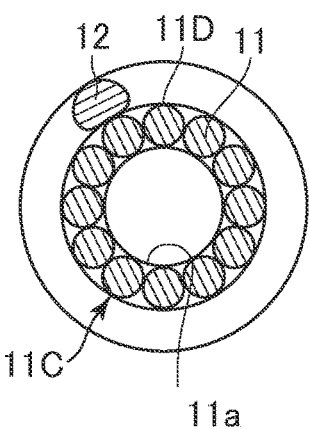
FIG. 2A is a cross-sectional view of the dilator of FIG. 1 cut in line IIA-IIA.

FIG. 1 is an overall configuration diagram of a dilator 1 according to an embodiment of the present disclosure. In FIG. 1, the left side in the drawing is the distal end side (far side) inserted into a body, and the right side in the drawing is the proximal end side (hand side, near side) operated by a technician such as a doctor. FIG. 2A is a cross-sectional view of the dilator 1 of FIG. 1 cut in line IIA-IIA, FIG. 2B is a cross-sectional view of the dilator 1 of FIG. 1 cut in line IIB-IIB, and FIG. 2C is a cross-sectional view of the dilator 1 of FIG. 1 cut in line IIC-IIC.

The dilator 1 includes a distal end side coil part 10, a proximal end side coil part 20, and a connector 2.

The distal end side coil part 10 is located at the most distal end side in the axial direction of the dilator 1, and includes a first coil 11 and a second coil 12. The second coil 12 is wound around an outer peripheral surface of the first coil 11. The wire forming the first coil 11 and the second coil 12 is, for example, a metal wire of a superelastic alloy or the like such as stainless steel or nickel-titanium, or a resin wire.

Figure 2B:
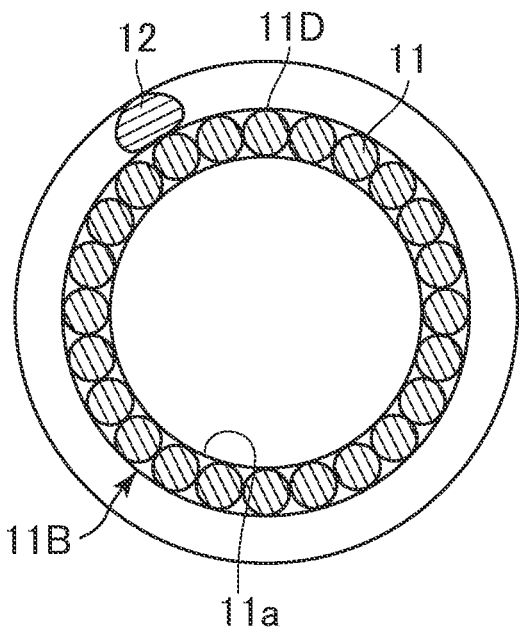
FIG. 2B is a cross-sectional view of the dilator of FIG. 1 cut in line IIB-IIB.
Figure 2C:
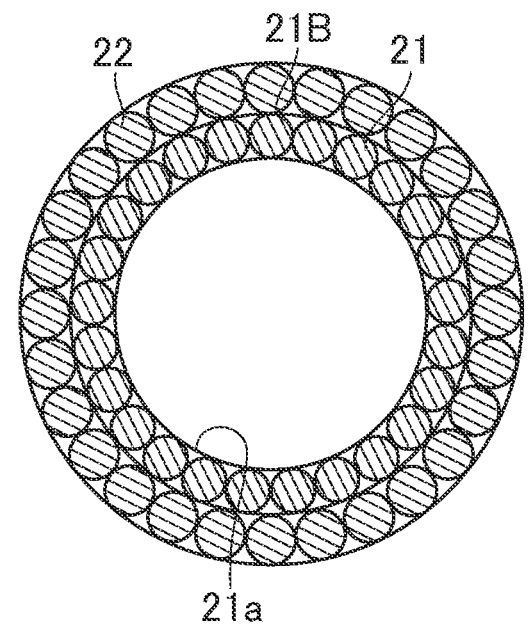
FIG. 2C is a cross-sectional view of the dilator of FIG. 1 cut in line IIC-IIC.

As illustrated in FIGS. 1, 2A, and 2B, the first coil 11 is formed by winding a plurality of (for example, 12) wires to have a hollow shape. The plurality of wires forming the first coil 11 are wound in a first winding direction. The first coil 11 has a lumen 11a penetrating the first coil 11 from the proximal end to the distal end. The first coil 11 has a straight portion 11B and a tapered portion 11C.

The straight portion 11B is located at the proximal end side of the first coil 11, and has a proximal end connected to the proximal end side coil part 20. The straight portion 11B has an outer diameter that is substantially constant from a proximal end to a distal end of the straight portion 11B. The tapered portion 11C is located at the distal end side of the straight portion 11B, extends from the distal end of the straight portion 11B to the distal end side, and is configured such that an outer diameter thereof becomes small toward the distal end side.

The second coil 12 is formed by winding, for example, one wire around an outer peripheral surface 11D of the first coil 11 in a second winding direction opposite to the first winding direction. In the present embodiment, the first winding direction is a direction of S-winding, and the second winding direction is a direction of Z-winding. The wire forming the second coil 12 is wound with a space. As a result, the outer peripheral surface 11D of the first coil 11 is provided with a spirally-arranged protruding portion projecting to the outside in the radial direction (the most outer surface, the most outside portion of the dilator 1). This spirally-arranged protruding portion has a gap in portions adjacent to each other (metal wires adjacent to each other) along the axis of the first coil 11. Due to a screw action of the spirally-arranged protruding portion, the dilator 1 can move forward also by a rotation operation of the dilator 1.

As illustrated in FIG. 1, the proximal end side coil part 20 is located at the proximal end side of the distal end side coil part 10, and includes a third coil 21 and a fourth coil 22. The fourth coil 22 is wound around an outer peripheral surface of the third coil 21. The proximal end of the proximal end side coil part 20 is connected with the connector 2. The wires forming the third coil 21 and the fourth coil 22 are each, for example, a metal wire of a superelastic alloy such as stainless steel or nickel-titanium, or a resin wire.

As illustrated in FIGS. 1 and 2C, the third coil 21 is formed by winding a plurality of (for example, 14) metal wires to have a hollow shape. The plurality of wires forming the third coil 21 are wound in the second winding direction. The third coil 21 has a lumen 21a penetrating the third coil 21 from a proximal end to a distal end, and has an outer diameter that is substantially constant from the proximal end to the distal end. The lumen 11a of the first coil 11 and the lumen 21a of the third coil 21 communicate with each other.

The fourth coil 22 is formed by winding a plurality of (for example, 14) wires around an outer peripheral surface 21B of the third coil 21 in the first winding direction. The diameter of the wires forming the fourth coil 22 is larger than the diameter of the wires forming the third coil 21. The outer diameter of the fourth coil 22 is almost equal to or slightly larger than the outer diameter of the second coil 12.

A plurality of wires forming the distal end portions and the proximal end portions of the first coil 11, the third coil 21, and the fourth coil 22 are welded over the entire peripheral direction of the first coil 11, the third coil 21, and the fourth coil 22 so that the wires (and thus the coils) do not separate from each other. The second coil 12 is welded to the first coil 11 in the distal end and the proximal end of the second coil 12, for example. The first coil 11 and the third coil 21 are formed of different wires from each other, and the second coil 12 and the fourth coil 22 are formed of different wires from each other.

The entire periphery of the proximal end portion 10A of the distal end side coil part 10 and the entire periphery of the distal end portion 20A of the proximal end side coil part 20 are welded to each other. As a result, a welded portion 3 is formed in a connection portion between the distal end side coil part 10 and the proximal end side coil part 20. The welded portion 3 has a tapered shape such that it tapers to the distal end side.

A length of the dilator 1 in the present embodiment and other embodiments described hereinafter is, for example, 2000 mm, and may be 1650 mm to 2350 mm. A length of the distal end side coil part 10 is, for example, 200 mm, and may be 50 to 400 mm. A length of the proximal end side coil part 20 is, for example, 1800 mm, and may be 1600 to 1950 mm. An inner diameter of the distal end of the first coil 11 is, for example, 0.7 mm, and may be 0.4 to 1.0 mm. An inner diameter of the proximal end of the first coil 11 and an inner diameter of the distal end of the third coil 21 are for example, 1.5 mm, and may be 1.0 to 3.0 mm. An outer diameter of the distal end of the second coil 12 is, for example, 1.84 mm, and may be 0.8 to 3.0 mm. An outer diameter of the proximal end of the second coil 12 is, for example, 2.64 mm, and may be 1.4 to 5.0 mm. A diameter of the metal wire of the first coil 11 and a diameter of the metal wire of the third coil 21 are for example, 0.21 mm, and may be 0.1 to 0.5 mm. A diameter of the metal wire of the second coil 12 and a diameter of the metal wire of the fourth coil 22 are for example, 0.36 mm, and may be 0.1 to 0.5 mm.

The connector 2 is a portion used by a technician for executing a rotation operation such as pushing the dilator 1 into a body or pulling the dilator 1 from the body. The distal end of the connector 2 is connected to the proximal end of the proximal end side coil part 20. The connector 2 is formed of, for example, a resin, and has a hollow shape having a lumen that communicates with the lumen 21a of the third coil 21.

Next, an example of the use mode of the dilator 1 is described as follows.

First, an object is punctured with an introducer needle to form a hole. Next, after insertion of a guide wire into a lumen of the introducer needle, the introducer needle is pulled out.

Next, a proximal end of the guide wire is inserted to the inner cavity of the dilator 1 to insert the dilator 1. Next, the dilator 1 is pushed to advance while rotating a shaft (distal end side coil part 10 and the proximal end side coil part 20) in the clockwise direction, to expand the hole of the punctured portion. At this time, since the tapered portion 11C moves forward due to a screw action or the like of the spirally-arranged protruding portion caused by the rotation operation of the shaft, the hole can be smoothly expanded by the tapered portion 11C. In order to move the dilator 1 rearward, the shaft is rotated in the counterclockwise direction.

In the dilator 1 of the present embodiment, the distal end side coil part 10 includes the first coil 11 formed by winding a wire in the first winding direction to have a hollow shape, and the second coil 12 provided on an outer periphery of the first coil 11 and formed by winding a wire in the second winding direction being an opposite winding direction to the first winding direction, and the proximal end side coil part 20 includes the third coil 21 formed by winding a wire in the second winding direction to have a hollow shape, and the fourth coil 22 provided on an outer periphery of the third coil 21 and formed by winding a wire in the first winding direction. The first winding direction is a direction of S-winding, and the second winding direction is a direction of Z-winding.

According to this configuration, when the dilator 1 is rotated in a direction of moving forward (clockwise. R direction in the drawing) due to a screw action of the first coil 11, in the distal end side coil part 10, a pitch of the first coil 11 decreases and the outer diameter of the first coil 11 decreases. In addition, a pitch of the second coil 12 increases and the outer diameter of the second coil 12 increases. As a result, when the dilator 1 is caused to advance in a constricted part while rotating in the clockwise direction, the second coil 12 expands in the radial direction and pushes and widens the constricted part, so that a performance of the dilator 1 of expanding the constricted part can be enhanced. On the contrary, in the proximal end side coil part 20, a pitch of the third coil 21 increases and the outer diameter of the third coil 21 increases. In addition, a pitch of the fourth coil 22 decreases and the inner diameter of the fourth coil 22 decreases. As a result, a force of the third coil 21 expanding in the radial direction and a force of the fourth coil 22 contracting in the radial direction interact with each other, and the wire of the third coil 21 and the wire of the fourth coil 22 closely contact with each other. Accordingly, torquability in the proximal end side coil part 20 can be enhanced. As described above, when the dilator 1 is rotated in the clockwise direction, by pushing and widening the constricted part in the radial direction by the distal end portion of the dilator 1, the expansion force for the constricted part can be increased, and high torquability can be obtained.

On the contrary, when the dilator 1 is rotated in a direction of moving rearward (counterclockwise direction), in the proximal end side coil part 20, a pitch of the third coil 21 decreases and the outer diameter of the third coil 21 decreases. In addition, a pitch of the fourth coil 22 increases and the outer diameter of the fourth coil 22 increases. On the contrary, in the distal end side coil part 10, a pitch of the first coil 11 increases and the outer diameter of the first coil 11 increases. In addition, a pitch of the second coil 12 decreases and the inner diameter of the second coil 12 decreases. As a result, a force of the first coil 11 expanding in the radial direction and a force of the second coil 12 contracting in the radial direction interact with each other, and the wire of the first coil 11 and the wire of the second coil 12 closely contact with each other. Accordingly, torquability in the distal end side coil part 10 can be enhanced, and in addition, by increasing the rigidity of the distal end side coil part 10, the performance of the dilator 1 of expanding the constricted part can be enhanced. As described above, when the dilator 1 is rotated in the counterclockwise direction, by increasing the rigidity of the distal end side, the performance of expanding the constricted part can be enhanced, and high torquability can be obtained.

As described above, according to the dilator 1 of the present embodiment, the performance of expanding the constricted part can be enhanced irrespective of the rotation direction of the dilator 1, and relatively high torquability can be obtained. The first winding direction is a direction of S-winding and the second winding direction is a direction of Z-winding, so that high torquability can be obtained in a normal use mode of the dilator 1.

The diameter of the wires forming the fourth coil 22 is larger than the diameter of the wires forming the third coil 21. As a result, the torque force of the proximal end side coil part 20 can be increased, and further, the torque force of the dilator 1 can be increased.

The entire periphery of the proximal end portion 10A of the distal end side coil part 10 and the entire periphery of the distal end portion 20A of the proximal end side coil part 20 are welded to each other. As a result, the force applied to the connector 2 of the dilator 1 can be reliably transmitted to the distal end side coil part 10.

The first coil 11 and the third coil 21 are formed of different wires from each other, and the second coil 12 and the fourth coil 22 are formed of different wires from each other. As a result, the distal end side coil part 10 and the proximal end side coil part 20 are separately formed and connected to each other, so that the dilator 1 can be easily manufactured.

Embodiments of the present disclosure has been described above. The present disclosure is not limited to these embodiments, and various modifications may be performed.

Figure 3:
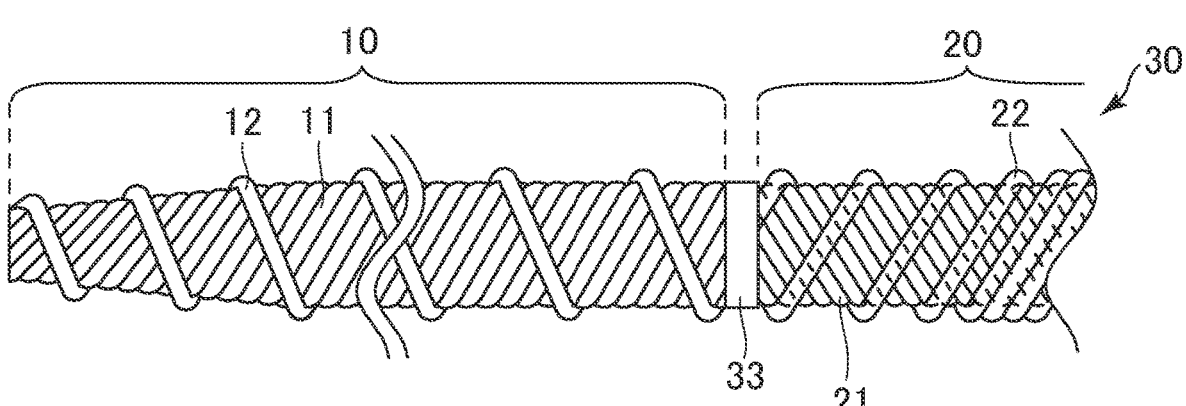
FIG. 3 is a diagram illustrating a distal end side portion of a dilator according to a modification.

For example, as a dilator 30 illustrated in FIG. 3, the wires forming the fourth coil 22 may be wound such that the wires in the distal end side are not in close contact so as to have a space, the spacing amount is gradually reduced toward the proximal end side, and the wires in close contact in the proximal end side. As a result, the rigidity of the dilator 30 can be gradually changed from the proximal end to the distal end. The welded portion 33 may not have a tapered shape, and may be configured such that the outer peripheral surface of the welded portion 33 is substantially parallel in the axial direction.

In the embodiments described above, the first coil 11 and the third coil 21 are formed of different wires from each other and the second coil 12 and the fourth coil 22 are formed of different wires from each other. However, the third coil 21 and the first coil 11 may be formed of the same wire and the fourth coil 22 and the second coil 12 may be formed of the same wire.

In the embodiments described above, the diameter of the metal wires forming the fourth coil 22 is larger than the diameter of the metal wires forming the third coil 21. However, the diameter of the metal wires forming the fourth coil 22 may be equal to or smaller than the diameter of the metal wires forming the third coil 21.

In the embodiments described above, the entire periphery of the proximal end portion 10A of the distal end side coil part 10 and the entire periphery of the distal end portion 20A of the proximal end side coil part 20 are welded to each other. However, the welding may be performed only at some positions (for example, four positions) in the outer periphery.

In the embodiments described above, the distal end side coil part 10 includes the straight portion 11B and the tapered portion 11C. However, the distal end side coil part 10 may not include the straight portion 11B. In addition, the distal end side coil part 10 may include a distal end portion in the distal end side of the tapered portion 11C, the distal end portion having an outer diameter that is substantially constant from the proximal end to the distal end.

In the embodiments described above, the first coil 11 and the fourth coil 22 are wound in the first winding direction (S-winding) and the second coil 12 and the third coil 21 are wound in the second winding direction (Z-winding). However, the first coil 11 and the fourth coil 22 may be wound in the second winding direction (Z-winding) and the second coil 12 and the third coil 21 may be wound in the first winding direction (S-winding).

According to this configuration, when the dilator 1 is rotated in a direction of moving forward (counterclockwise direction) due to a screw action of the first coil 11, in the distal end side coil part 10, a pitch of the first coil 11 decreases and the outer diameter of the first coil 11 decreases. In addition, a pitch of the second coil 12 increases and the outer diameter of the second coil 12 increases. As a result, when the dilator 1 is caused to advance in a constricted part while rotating in the counterclockwise direction, the second coil 12 expands in the radial direction and pushes and widens the constricted part, so that a performance of the dilator 1 of expanding the constricted part can be enhanced. On the contrary, in the proximal end side coil part 20, a pitch of the third coil 21 increases and the outer diameter of the third coil 21 increases. In addition, a pitch of the fourth coil 22 decreases and the inner diameter of the fourth coil 22 decreases. As a result, a force of the third coil 21 expanding in the radial direction and a force of the fourth coil 22 contracting in the radial direction interact with each other, and the wire of the third coil 21 and the wire of the fourth coil 22 closely contact with each other. Accordingly, torquability in the proximal end side coil part 20 can be enhanced. As described above, when the dilator 1 is rotated in the counterclockwise direction, by pushing and widening the constricted part in the radial direction by the distal end portion of the dilator 1, the expansion force in the constricted part can be increased, and high torquability can be obtained.

On the contrary, when the dilator 1 is rotated in a direction of moving rearward (clockwise direction), in the proximal end side coil part 20, a pitch of the third coil 21 decreases and the outer diameter of the third coil 21 decreases. In addition, a pitch of the fourth coil 22 increases and the outer diameter of the fourth coil 22 increases. On the contrary, in the distal end side coil part 10, a pitch of the first coil 11 increases and the outer diameter of the first coil 11 increases. In addition, a pitch of the second coil 12 decreases and the inner diameter of the second coil 12 decreases. As a result, a force of the first coil 11 expanding in the radial direction and a force of the second coil 12 contracting in the radial direction interact with each other, and the wire of the first coil 11 and the wire of the second coil 12 closely contact with each other. Accordingly, torquability in the distal end side coil part 10 can be enhanced, and in addition, by increasing the rigidity of the distal end side coil part 10, the performance of the dilator 1 of expanding the constricted part can be enhanced. As described above, when the dilator 1 is rotated in the clockwise direction, by increasing the rigidity of the distal end side, the performance of expanding the constricted part can be enhanced, and high torquability can be obtained.

The number of wires of the first coil 11 and the third coil 21 is not limited to the number described above, and may be one or a plurality. The number of wires of the second coil 12 may be a plurality. The number of wires of the fourth coil 22 is not limited to the number described above, and may be one or a plurality.

What is claimed is:

1. A dilator comprising:
a distal end side coil part comprising:
  a first coil having a hollow shape and comprising a first wire wound in a first winding direction; and
  a second coil provided around an outer periphery of the first coil and comprising a second wire wound in a second winding direction that is opposite to the first winding direction; and
a proximal end side coil part located at a proximal end side of the distal end side coil part and having a distal end portion connected to a proximal end portion of the distal end side coil part, the proximal end side coil part comprising:
  a third coil having a hollow shape and comprising a third wire wound in the second winding direction; and
  a fourth coil provided around an outer periphery of the third coil and comprising a fourth wire wound in the first winding direction.

2. The dilator according to claim 1, wherein:
the first winding direction is a direction of S-winding, and the second winding direction is a direction of Z-winding.

3. The dilator according to claim 1, wherein a weld connecting the distal end side coil part and the proximal end side coil part is formed between an entire periphery of the proximal end portion of the distal end side coil part and an entire periphery of the distal end portion of the proximal end side coil part.

4. The dilator according to claim 1, wherein:
the first wire and the third wire are different wires from each other, and
the second wire and the fourth wire are different wires from each other.

5. The dilator according to claim 1, wherein:
in the distal end side coil part, the first coil is an innermost coil and the second coil is an outermost coil, and
in the proximal end side coil part, the third coil is an innermost coil and the fourth coil is an outermost coil.

6. A dilator comprising:
a distal end side coil part comprising:
  a first coil having a hollow shape and comprising a first wire wound in a first winding direction; and
  a second coil provided around an outer periphery of the first coil and comprising a second wire wound in a second winding direction that is opposite to the first winding direction; and
a proximal end side coil part located at a proximal end side of the distal end side coil part and having a distal end portion connected to a proximal end portion of the distal end side coil part, the proximal end side coil part comprising:
  a third coil having a hollow shape and comprising a third wire wound in the second winding direction; and
  a fourth coil provided around an outer periphery of the third coil and comprising a fourth wire in the first winding direction,
  wherein a weld connecting the distal end side coil part and the proximal end side coil part is formed between an entire periphery of the proximal end portion of the distal end side coil part and an entire periphery of the distal end portion of the proximal end side coil part,
  wherein a lumen of the first coil and a lumen of the third coil are in communication with each other.

7. The dilator according to claim 6, wherein:
the first winding direction is a direction of S-winding, and
the second winding direction is a direction of Z-winding.

8. The dilator according to claim 6, wherein:
the first wire and the third wire are different wires from each other, and the second wire and the fourth wire are different wires from each other.

9. The dilator according to claim 6, wherein:
the diameter of the wires forming the fourth coil is larger than the diameter of the wires forming the third coil.

\* \* \* \* \*